United States Patent
Sogaro

(10) Patent No.: US 7,465,119 B2
(45) Date of Patent: Dec. 16, 2008

(54) APPLICATION DEVICE

(75) Inventor: Alberto C. Sogaro, Kronberg (DE)

(73) Assignee: Dentaco Dentalindustrie Und-Marketing GmbH, Bad Homburg (DE)

( * ) Notice: Subject to any disclaimer, the term of this patent is extended or adjusted under 35 U.S.C. 154(b) by 6 days.

(21) Appl. No.: 11/676,384

(22) Filed: Feb. 19, 2007

(65) Prior Publication Data

US 2007/0196159 A1    Aug. 23, 2007

(30) Foreign Application Priority Data

Feb. 23, 2006   (DE)   ............. 20 2006 002 926 U

(51) Int. Cl.
 *A47L 13/22*   (2006.01)
 *B43M 11/06*   (2006.01)
(52) U.S. Cl. ............ 401/280; 401/183; 401/188 R
(58) Field of Classification Search ......... 401/183, 401/184, 185, 186, 280, 281, 152, 188 R; 222/213, 492, 495
See application file for complete search history.

(56) References Cited

U.S. PATENT DOCUMENTS

| | | | | |
|---|---|---|---|---|
| 5,290,105 | A * | 3/1994 | Tencati | ............ 383/203 |
| 6,227,736 | B1 | 5/2001 | Sogaro | |
| 6,405,905 | B1 | 6/2002 | Sogaro | |
| 6,447,476 | B1 | 9/2002 | Sogaro | |
| 6,547,101 | B1 | 4/2003 | Sogaro | |
| 6,613,021 | B2 | 9/2003 | Sogaro | |
| 6,719,729 | B2 | 4/2004 | Sogaro | |
| 7,100,802 | B2 | 9/2006 | Sogaro | |
| 2004/0223802 | A1 * | 11/2004 | Bergey et al. | ............ 401/133 |

FOREIGN PATENT DOCUMENTS

| | | | |
|---|---|---|---|
| DE | 1063340 | A | 8/1959 |
| DE | 2638200 | A1 | 3/1978 |
| DE | 3718326 | A1 | 12/1988 |
| DE | 9107574 | U1 | 9/1991 |
| DE | 42 23 689 | * | 1/1993 |
| DE | 19722765 | A1 | 3/1998 |
| DE | 20019091 | U1 | 5/2001 |

OTHER PUBLICATIONS

European Search Report, Apr. 2006.

* cited by examiner

*Primary Examiner*—David J Walczak
(74) *Attorney, Agent, or Firm*—Quarles & Brady LLP

(57) ABSTRACT

An application device includes an applicator unit (12) which is provided with an applicator (14) and which has a cylindrical peg (18) on the side facing away from the applicator (14), which is penetrated by a cross channel (26), from which an axial channel (28) branches off, which leads to the applicator (14), in which a shiftable reservoir (30) is arranged. The reservoir (30) has an annular lip seal (38) which interacts as a seal with the cylindrical peg (18). The activation of the application device occurs by shifting the reservoir (30) on the cylindrical peg (18) in the direction of the applicator (14). The reservoir (30) has a foldable, bag-like, deformable receiver section (34), so that when a flow connection between the application device and the cross channel (26) and the receiver section (34) is established in the activation position, the flowable substance is discharged via the applicator (14) through manual deformation of the bag-like receiver section (34).

20 Claims, 2 Drawing Sheets

APPLICATION DEVICE

CROSS REFERENCES TO RELATED APPLICATIONS

This application claims the priority benefit of German Utility Model No. 20 2006 002 926.5 filed on Feb. 23, 2006

STATEMENT REGARDING FEDERALLY SPONSORED RESEARCH

Not Applicable.

DESCRIPTION OF THE BACKGROUND ART

The invention relates to an application device for a flowable substance. Known application devices include an applicator unit having a reservoir and an applicator. The application is provided on one end of a cylindrical peg. An opposing end of the peg extends into the reservoir for receiving a flowable substance. The opposing end of the peg is penetrated by a cross channel from which an axial channel branches off and leads to the applicator. At least one annular lip seal of the applicator unit interacts as a seal with the cylindrical peg of the application device, whereby an activation of the application device occurs by shifting the reservoir on the cylindrical peg in the direction of the applicator, i.e. the peg is inserted further into the reservoir.

An application device of this type is known from DE 200 19 091 U1 and serves particularly for the application of pharmaceutical or cosmetic substances onto the human body. The known application device is designed in the form of a mini-syringe which has a cannula-shaped tip as applicator with which the flowable substance can be discharged. For activation, the reservoir, which is designed cup-shaped or like a small tube which is closed on one side, is manually shifted on the cylindrical peg so that the peg acts like a piston that displaces the flowable substance stored in the reservoir and delivers it via the cross channel and the axial channel of the application unit to the application tip. During the activation, the side wall of the reservoir penetrates the annular recess surrounding the peg. The application device known from DE 200 19 091 U1 has the disadvantage that accurate metering of the flowable substance is not possible without problems, since the controlled shifting of the tubular shaped reservoir on the cylindrical peg is difficult.

SUMMARY OF THE INVENTION

One object of the invention is to create an application device in accordance with the type mentioned in the introduction, which distinguishes itself through improved metering characteristics with respect to state-of-the-art technology. In one embodiment incorporating the present invention, the object of the invention is solved by providing an application device having a reservoir with a bag-like, deformable receiver section, which, in the activation position of the application device, in which the lip seal is located on the side of the openings of the cross channel of the cylindrical peg facing away from the side of the storage section and consequently a flow connection between the receiver section and the cross channel exists, and can be manually deformed in such a way that the flowable substance can be discharged via the application device. The discharge of the flowable substance via the application device occurs by manual deformation of the receiver section, after the activation, i.e. after the shifting of the reservoir on the cylindrical peg. An additional displacement of the reservoir on the cylindrical peg is not required for this. The peg therefore does not act as a displacement piston for the flowable substance.

In a preferred embodiment of this application device according to the invention, the bag-like receiver section is created by two film cut-outs which are sealed together along their edges. Depending on the application, such film cut-outs can be easily manufactured and adapted to the volume to be procured.

In another embodiment of the present invention, the application device for a flowable substance includes an applicator unit which is provided with an applicator and which has a cylindrical peg on the side facing away from the applicator unit, which is penetrated by a cross channel, from which an axial channel branches off, which leads to the applicator, in which a reservoir is arranged on the cylindrical peg so it can be shifted, which has one annular lip seal that interacts as a seal with the cylindrical peg, in which the activation of the application device occurs by shifting the reservoir on the cylindrical peg in the direction of the applicator unit in order to open a flow connection between the reservoir and the cross channel. The reservoir has a receiver section which has a pump unit, so that when the application unit is in the activation position, a flow connection between the cross channel and the receiver section is established, and the flowable substance is discharged via the applicator by actuation of the pump unit.

The application device incorporating the present invention is particularly suitable for the application of pharmaceutical or cosmetic substances onto human or animal bodies, in which case it can be provided with an applicator that has been adapted for the respective specific application. The applicator can, for example, constitute a pipette tip, or also comprise a brush, a mop, or a small sponge. The applicator can also comprise a dispenser which can be provided with a spoon-shaped receiver area.

A pharmaceutical substance, which can be applied by means of the device according to the invention, can for example be a tissue adhesive, a dental adhesive, or suchlike.

The application device incorporating the present invention is particularly designed as a disposable device in which the reservoir has been pre-filled. In the deactivated state, which represents a blocked position, the flowable substance is retained in the reservoir, secured by the lip seal. As a rule, this is the state in which the application device is delivered. The blocked position can be secured by means of a detent mechanism, a detachable Velcro tab or the like. In order to activate the application device, the user pushes together the application unit and the reservoir of the application device like a telescope, so that a transition from the closed storage position to the open dispensing position and/or activation position of the applicator with respect to the applicator occurs. During activation, the lip seal wipes across the openings of the cross channel in the peg. The telescoping action occurs, for example, by rotating the applicator with the help of a thread or a bayonet-like coupling.

In order to ensure the secure guidance of the peg in the reservoir, the reservoir in a preferred embodiment of the application device according to the invention has a rigid guide insert, which has a bore for guiding the peg of the applicator unit. The lip seal is also arranged on the wall of the bore. The guide insert is preferably also sealed with the bag-like receiver section. In order to ensure peripheral sealing in the area of the guide insert, it is useful if the guide insert essentially has converging wedge-shaped edges.

In order to prevent the peg from shifting into the de-activation position during the discharge of the flowable substance from the reservoir, it is useful to provide a detent mechanism which secures the peg in the activation position. Such detent mechanism comprises, for example, a peg which can be screwed into a ring groove of the reservoir to secure the activation position. Particularly in this case, the peg is spring-loaded so that upon loosening of the detent mechanism it will be automatically shifted into the deactivation position.

The applicator unit can furthermore be provided with an operating and/or gripper element, such as a strap, a collar, or suchlike, which can be fluted or similar.

In order to provide users haptic information regarding the respective activation and/or deactivation position, the cylindrical peg can have at least one ring groove which will interact with the lip seal to define the deactivation position and/or activation position of the reservoir with reference to the applicator unit.

The device incorporating the present invention can also be designed to discharge a multicomponent system in which the components must be mixed during application. In this case, the reservoir has two or even more chambers. The chambers can be separated from each other by a detachable seal seam which can be burst apart and/or detached by the application of manual pressure before the device is activated, giving the components that are stored in the individual chambers the opportunity to mix within the receiver unit. It is also conceivable that the components can mix in the area of the applicator after the device has been activated.

Additional advantages and advantageous embodiments of the subject matter of the invention can be found in the description, in the drawing, and in the Claims.

BRIEF SUMMARY OF THE DRAWINGS

An embodiment of the application device according to the invention is shown in the drawing in a simplified schematic representation and is explained in detail in the following description.

DETAILED DESCRIPTION OF THE PREFERRED EMBODIMENTS

Figure 1:
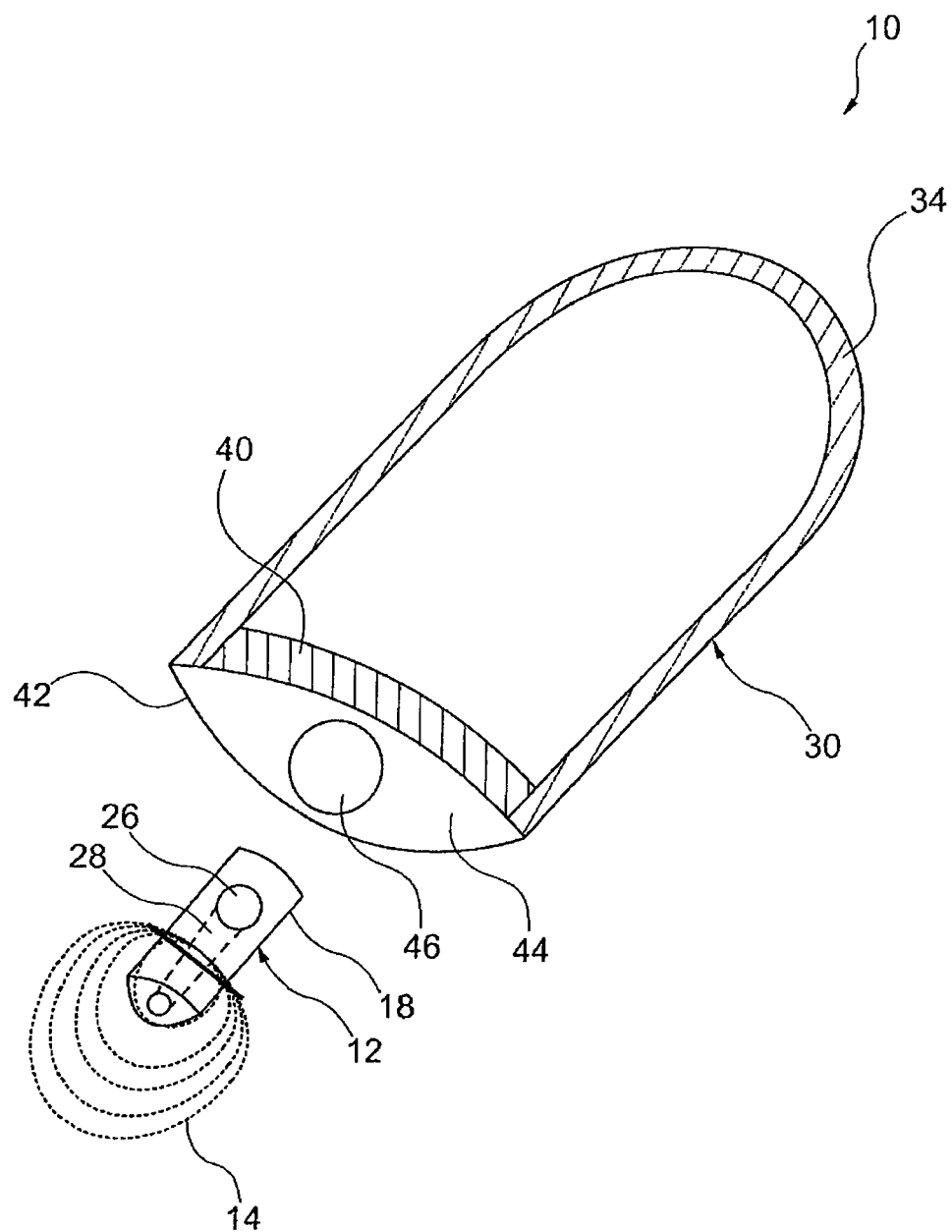
FIG. 1 shows a perspective view of an application device for a one-component system.
Figure 2:
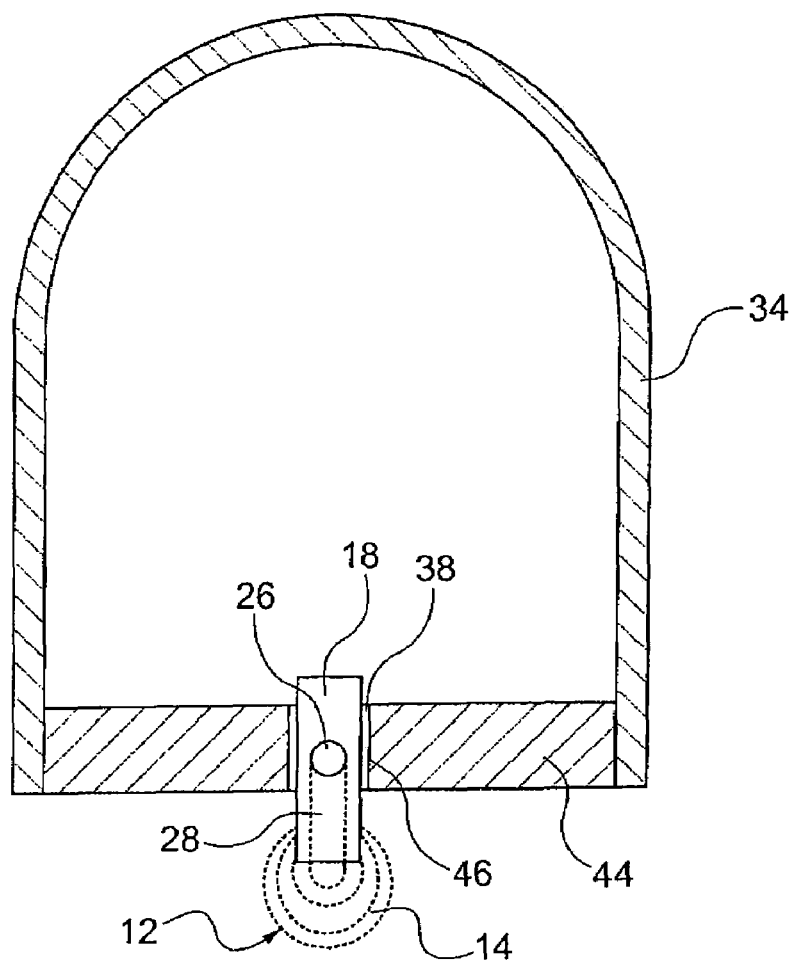
FIG. 2 shows a section along the center plane of the application device according to FIG. 1, which is in the deactivation position.

FIGS. 1 and 2 show an application device 10, which, for example, is for the application of a flowable substance and which comprises an applicator unit 12 on which the applicator 14 has been designed as a mop and/or sponge. On the side facing away from the applicator 14, the applicator unit 12 has a cylindrical, piston-like peg 18. In the end section facing away from the applicator 14, the peg 18 is penetrated by a cross channel 26 which extends in a radial direction. An axial channel 28 coaxial with the axis of peg 18, branches off and extends up to the applicator 14 from cross channel 26.

The application device 10 includes a reservoir 30, in which the flowable substance can be stored. The reservoir 30 comprises a bag-like receiver section 34, in which the flowable substance is stored and which is created by two film cut-outs 40, 42 which are sealed together along their edges.

On the side facing the applicator unit 12, the reservoir 30 has a rigid guide insert 44 which essentially has converging wedge-shaped edges and is sealed with the two film cut-outs 40, 42. The guide insert 44 has a bore 46, which has an annular lip seal 38 on its inside wall, which is configured so as to slide along the circumferential surface of the cylindrical peg 18.

In the deactivation position of the reservoir 30 shown in FIG. 2, the lip seal 38 is positioned in the end section of the circumferential surface of peg 18, so that the fluid flow between the receiver section 34 and the cross channel 26 is blocked.

Figure 3:
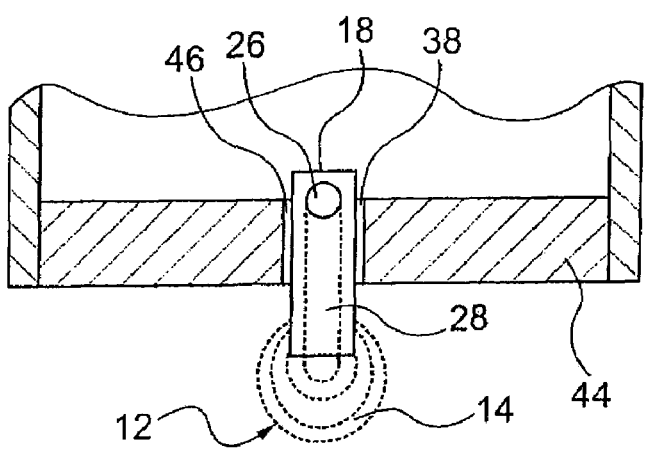
FIG. 3 shows a section along the center plane of the application device according to FIG. 1, which is in the activation position.

In order to activate the application device 10, the reservoir 30 is brought into its open dispensing position, represented in FIG. 3. In this process, the applicator unit 12 and the reservoir 30 are telescoped, so that the lip seal 38 moves across the transverse bore and through the annular clearance between the cylindrical peg 18 and the inside wall of bore 46 of the insert 44 of the reservoir 30, creating a flow connection between the bag-like receiver section 34 and the cross channel 26. Through manual deformation and/or by applying pressure on the receiver section 34, the stored flowable substance is expelled from the receiver section 34 and is then delivered via the cross channel 26 and the axial channel 28 to the applicator 14 for application.

I claim:

1. An application device for a flowable substance, comprising
an applicator unit (12) which is provided with an applicator (14) and which has a cylindrical peg (18) on a side facing away from the applicator (14), which is penetrated by a cross channel (26), from which an axial channel (28) branches off, which leads to the applicator (14), on said applicator unit (12), a shiftable reservoir (30) being arranged, which has an annular lip seal (38) which acts as a seal together with the cylindrical peg (18), in which activation of the application device occurs by shifting the reservoir (30) on the cylindrical peg (18) toward the applicator (14) to an activation position in order to open a flow connection between the reservoir (30) and the cross channel (26), wherein the reservoir (30) has a foldable, bag-like, deformable receiver section (34), so that when a flow connection between the application device and the cross channel (26) and the receiver section (34) is established in the activation position, the flowable substance is discharged via the applicator (14) through manual deformation of the foldable, bag-like receiver section (34).

2. The application device as in claim 1, wherein the bag-like receiver section (34) is created by two film cut-outs (40, 42) which are sealed together along their edges.

3. The application device as in claim 1, wherein the reservoir (30) has a rigid guide insert (44) in which a bore (46) for guiding the peg (18) of the applicator unit (12) is arranged.

4. The application device as in claim 3, wherein the guide insert (44) is sealed with a bag-like receiver section (34).

5. The application device as in claim 3, wherein the guide insert (44) essentially has converging wedge-shaped edges.

6. The application device as in claim 1, characterized by a detent mechanism which secures the peg in the activation position.

7. The application device as in claim 6, wherein the detent mechanism comprises a peg which can be screwed into an annular groove of the reservoir in order to secure the activation position.

8. The application device as in claim 1, wherein the cylindrical peg (18) has at least one annular groove which interacts with the lip seal (38) and defines a de-activation position and/or an activation position of the reservoir.

9. An application device for a flowable substance, comprising an applicator unit (12) which is provided with an applicator (14) and which has a cylindrical peg (18), which is penetrated by a cross channel (26), from which an axial channel (28) branches off, which leads to the applicator (14), on said applicator unit (12), a shiftable reservoir (30) being arranged, which has an annular lip seal (38) which interacts as a seal with the cylindrical peg (18), in which activation of the application device occurs by shifting the reservoir (30) on the cylindrical peg (18) toward the applicator (14) to an activation position in order to open a flow connection between the reservoir (30) and the cross channel (26), wherein the reservoir (30) has a receiver section (34) provided with a pump device, so that when a flow connection between the application unit and the cross channel (26) and the receiver section (34) is established in the activation position, the flowable substance is discharged via the applicator (14) by actuation of the pump device.

10. The application device as in claim 9, wherein the reservoir (30) has a rigid guide insert (44) in which a bore (46) for guiding the peg (18) of the applicator unit (12) is arranged.

11. The application device as in claim 10, wherein the guide insert (44) is sealed with a bag-like receiver section (34).

12. The application device as in claim 10, wherein the guide insert (44) essentially has converging wedge-shaped edges.

13. The application device as in claim 9, characterized by a detent mechanism which secures the peg in the activation position.

14. The application device as in claim 13, wherein the detent mechanism comprises a peg which can be screwed into an annular groove of the reservoir in order to secure the activation position.

15. The application device as in claim 9, wherein the cylindrical peg (18) has at least one annular groove which interacts with the lip seal (38) and defines a de-activation position and/or an activation position of the reservoir.

16. An application device for a flowable substance, said device comprising
    an applicator unit defining a reservoir for holding a flowable substance, said reservoir having a foldable, bag-like receiver section;
    a bore in fluid communication with said receiver section, said bore including an annular seal;
    a peg slidably received in said bore and engaging said annular seal, said peg including a cross channel formed at one end received through said bore and an axial channel branching off from said cross channel; and
    an applicator disposed at a second end of said peg and in fluid communication with said axial channel, wherein activation of the application device occurs by sliding said peg into the reservoir to an activation position in order to open a flow connection between the reservoir and the cross channel and the flowable substance is discharged via the applicator through manual deformation of the foldable, bag-like receiver section.

17. The application device as in claim 16, wherein the foldable, bag-like receiver section is created by two film cut-outs which are sealed together along their edges.

18. The application device as in claim 16, wherein the reservoir has a rigid guide insert in which a bore for guiding the peg of the applicator unit is arranged.

19. The application device as in claim 16, characterized by a detent mechanism which secures the peg in the activation position.

20. The application device as in claim 16, wherein the peg has at least one annular groove which interacts with the annular seal and defines a de-activation position and/or an activation position of the reservoir.

* * * * *

UNITED STATES PATENT AND TRADEMARK OFFICE
CERTIFICATE OF CORRECTION

PATENT NO. : 7,465,119 B2 Page 1 of 1
APPLICATION NO. : 11/676384
DATED : December 16, 2008
INVENTOR(S) : Alberto C. Sogaro It is certified that error appears in the above-identified patent and that said Letters Patent is hereby corrected as shown below:

Column 4, Lines 23-24, Claim 1, "compnsing" should be changed to -- comprising --

Signed and Sealed this

Nineteenth Day of May, 2009

JOHN DOLL
*Acting Director of the United States Patent and Trademark Office*